(12) United States Patent
Vankipuram et al.

(10) Patent No.: US 11,543,884 B2
(45) Date of Patent: Jan. 3, 2023

(54) HEADSET SIGNALS TO DETERMINE EMOTIONAL STATES

(71) Applicant: Hewlett-Packard Development Company, L.P., Spring, TX (US)

(72) Inventors: Mithra Vankipuram, Palo Alto, CA (US); Sarthak Ghosh, Palo Alto, CA (US); Kevin Lee Smathers, Palo Alto, CA (US); Rafael Antonio Ballagas, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 17/414,343

(22) PCT Filed: Jun. 14, 2019

(86) PCT No.: PCT/US2019/037199
§ 371 (c)(1),
(2) Date: Jun. 16, 2021

(87) PCT Pub. No.: WO2020/251585
PCT Pub. Date: Dec. 17, 2020

(65) Prior Publication Data
US 2022/0091670 A1 Mar. 24, 2022

(51) Int. Cl.
*G06F 3/01* (2006.01)
(52) U.S. Cl.
CPC .............. *G06F 3/015* (2013.01); *G06F 3/013* (2013.01); *G06F 2203/011* (2013.01)

(58) Field of Classification Search
CPC ....... A61B 5/165; A61B 5/163; A61B 5/1128; A61B 5/6803; A61B 5/7282; G06F 3/015; G06F 3/011; G06F 3/013
See application file for complete search history.

(56) References Cited

U.S. PATENT DOCUMENTS

| | | |
|---|---|---|
| 6,151,571 A | 11/2000 | Pertrushin |
| 8,209,182 B2 | 6/2012 | Narayanan |

(Continued)

FOREIGN PATENT DOCUMENTS

| | | |
|---|---|---|
| EP | 3096208 A1 | 11/2016 |
| JP | 2017021737 A * | 1/2017 |

(Continued)

OTHER PUBLICATIONS

Busso, Carlos et al., "Analysis of Emotion Recognition using Facial Expressions, Speech and Multimodal Information", Oct. 13, 2004, ACM, 7 pages.

(Continued)

*Primary Examiner* — Hang Lin
(74) *Attorney, Agent, or Firm* — Quarles & Brady LLP

(57) ABSTRACT

An example non-transitory machine-readable medium includes instructions executable by a processor to capture a biometric signal from a biometric sensor at a headset that includes a stereoscopic display, capture a facial motion signal from a facial motion sensor associated with the headset, determine facial movement of a wearer of the headset based on the facial motion signal, apply a weight to the biometric signal based on the facial movement to obtain a weighted biometric signal, and use the weighted biometric signal to determine an emotional state of the wearer.

15 Claims, 7 Drawing Sheets

(56) References Cited

U.S. PATENT DOCUMENTS

| | | |
|---|---|---|
| 9,031,293 B2 | 5/2015 | Kalinli-Akbacak |
| 10,120,413 B2 | 11/2018 | Aimone et al. |
| 2011/0134026 A1 | 6/2011 | Kang et al. |
| 2011/0137137 A1 | 6/2011 | Shin et al. |
| 2013/0144937 A1 | 6/2013 | Lee |
| 2014/0022370 A1 | 1/2014 | Sohn et al. |
| 2016/0042648 A1 | 2/2016 | Kothuri |
| 2016/0147068 A1* | 5/2016 | Wei .................. G02B 27/4211 359/633 |
| 2016/0259977 A1 | 9/2016 | Asbun et al. |
| 2017/0060256 A1 | 3/2017 | Heck et al. |
| 2017/0160813 A1 | 6/2017 | Divakaran et al. |
| 2017/0259167 A1 | 9/2017 | Cook et al. |
| 2017/0337742 A1 | 11/2017 | Powderly et al. |
| 2018/0315063 A1* | 11/2018 | Cheesman ............ A61B 5/165 |

FOREIGN PATENT DOCUMENTS

| | | |
|---|---|---|
| KR | 101633057 | 6/2016 |
| WO | WO-2007098560 A1 | 9/2007 |
| WO | WO-2015051660 A1 | 4/2015 |
| WO | WO-2017156570 | 9/2017 |

OTHER PUBLICATIONS

Mehta, Dhwani et al., "Facial Emotion Recognition A Survey and Real-World User Experiences in Mixed Reality", Feb. 1, 2018, Sensors 2018, 18, 416. 24 pages.

* cited by examiner

HEADSET SIGNALS TO DETERMINE EMOTIONAL STATES

BACKGROUND

Virtual reality (VR), augmented reality (AR), mixed reality (MR), and similar technologies may be used to immerse people in computer-facilitated experiences. Examples of immersive computer-facilitated experiences include simulation, training, videoconferencing, and location-based entertainment. A headset may be used to communicate visual information to a person to facilitate such experiences.

DETAILED DESCRIPTION

Figure 1:
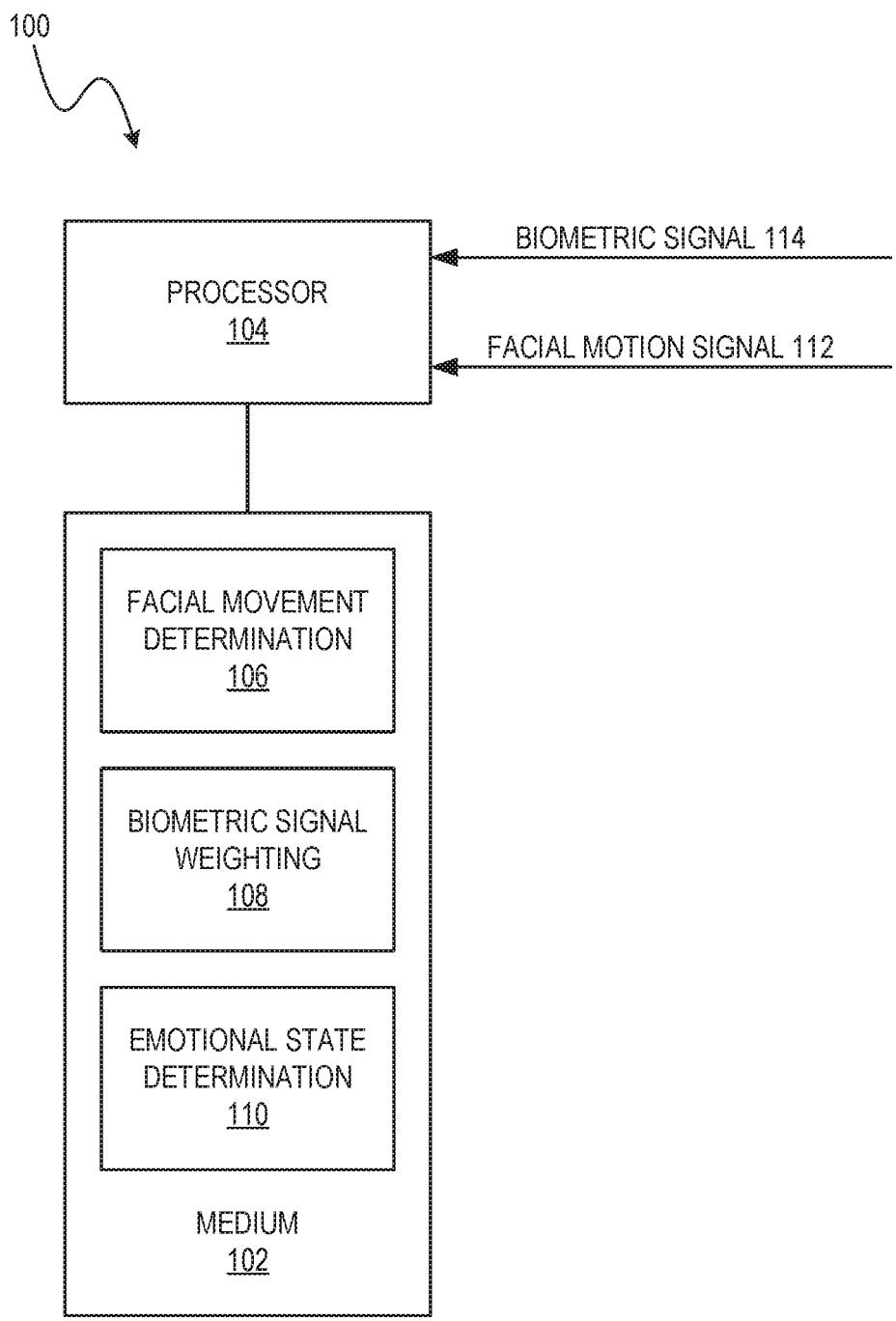
FIG. 1 is a block diagram of an example device to determine emotional state from a headset wearer's facial movement and a biometric sensor at a headset.

Detection of emotion during a VR, AR, MR, or similar experience (hereinafter referred to as "extended reality" or "XR" for clarity) may be useful to determine whether a simulation or training experience is having the intended effect. Emotion detection may help determine cognitive/mental load, and the effectiveness of a training or simulation experience may increase if cognitive/mental load is controlled. For example, in a training experience, detection of a negative emotion (e.g., anger, sadness, or disgust) may indicate that the individual being trained is being overloaded or did not fully understand the subject matter of the training.

Communication of emotion in an XR experience may be prone to error, which may lead to misunderstanding or miscommunication. For example, in an XR-facilitated videoconference, expression of emotion by participants may be limited by the fidelity of the communicated speech and the visual representations of user avatars. Social cues and nuance may be lost, which may unpredictably alter the course of a conversation.

A camera may be used to capture images of a person's face during an XR experience and such images may be used to detect emotion. However, an XR headset may obstruct key areas of the person's face, such as the eyes and area around the eyes.

A biometric sensor may be used to determine a person's emotional state when the person is wearing a headset. An electromyography (EMG) sensor may be provided to the gasket of the headset. A microphone may be provided to the headset to capture the wearer's vocalizations, such as speech. A camera may be attached to the headset and aimed at the wearer's lip and jaw area. An eye sensor may be provided to the headset to track the wearer's pupil dilation, eye movement, or eyelid movement. Captured sensor information may be used to determine the wearers emotional state, such as by using action units (AUs), speech analysis, an artificial neural network (ANN), or similar.

A motion sensor, such as the camera or microphone, may be used to detect motion of the headset wearer's face. Emotional state may then be determined using biometric sensor data that is weighted in view of the motion or lack of motion of the wearer's face. Motion blur detection may be used. For example, emotional state determination, including EMG signal analysis, may be delayed until a user stops speaking, as may be indicated by a relatively low degree of motion in images of the users lips and jaw. In another example, vocalization may be given increased influence on emotional state determination when it is determined that the wearer is vocalizing, as may be indicated by a relatively high degree of motion in images of the users lips and jaw. In still another example, a vocalization signal may signify face motion that reduces the value of an electromyography signal or lip/jaw image but that increases the significance of speech analysis.

Use of motion data of the user's face to facilitate the processing of data from biometric sensors may increase accuracy of emotion detection, assist in determining cognitive/mental load, and reduce instances of miscommunication or misunderstanding in XR experiences.

FIG. 1 shows an example device 100 to determine emotional state based on a headset wearer's facial movement. The device 100 may be provided to a headset, for example, as part of an integrated circuit in the headset. An example headset includes a stereoscopic display and may be an XR headset, AR headset, MR headset, or similar type of headset. In other examples, the device 100 may be external to the headset, for example, the device 100 may be provided to a computing device to which the headset may be connected. In still other examples, a component of the device 100 may be provided to the headset and another component of the device 100 may be provided to a computing device to which the headset may be connected.

The device 100 includes a non-transitory machine-readable medium 102. The medium 102 may be an electronic, magnetic, optical, or other physical storage device that encodes executable instructions. The medium 102 may include, for example, random access memory (RAM), read-only memory (ROM), electrically-erasable programmable read-only memory (EEPROM), flash memory, a storage drive, an optical disc, or similar.

The device 100 may include a processor 104 that may be connected to the non-transitory machine-readable medium 102. The processor 104 may include a central processing unit (CPU), a microcontroller, a microprocessor, a processing core, a field-programmable gate array (FPGA), or a similar device capable of executing instructions. The processor 104 and medium 102 may cooperate to execute instructions.

The device 100 includes a set of instructions stored in the non-transitory machine-readable medium 102. The instructions may include facial movement determination instructions 106, biometric signal weighting instructions 108, and emotional state determination instructions 110. The instructions 106, 108, 110 may be subsets of a contiguous set of instructions and may be considered separate components for sake of explanation.

The facial movement determination instructions 106 determine facial movement of a wearer of a headset based on a facial motion signal 112 that is captured by a camera, electromyographic sensor, microphone, or similar facial motion sensor associated with the headset. It is contemplated that facial motion of the wearer of the headset may be directly measured by a camera, or similar sensor, or may be implicitly measured by microphone, or similar sensor. A camera may be installed on the headset and aimed towards an uncovered part of the wearer's face, such as the lip and jaw area. A microphone may be installed on the headset in the vicinity of the wearer's mouth. The facial movement determination instructions 106 may determine the presence or absence of facial movement, as compared to a threshold amount of movement, or may determine a degree of facial movement, such as a numerical value on a predefined scale. In the example of a camera, image analysis techniques, such as feature extraction and motion blur detection may be used. In the example of a microphone, audio signal analysis may be used.

The biometric signal weighting instructions 108 apply a weight to a biometric signal 114 based on the facial movement determined from analysis of the facial motion signal 112. The biometric signal 114 may be captured from a sensor, such as a camera, a microphone, an electromyography sensor, an eye sensor, a physiological sensor, or a similar biometric sensor, located at the headset. For example, an electromyography sensor may be provided to the headset so that the sensor is in contact with the wearer's skin around the eye. Any number and type of biometric signals 114 may be captured.

The sensor used to capture the facial motion signal 112 may also be used to capture a biometric signal 114. The facial motion signal may inherently be a biometric signal.

The biometric signal weighting instructions 108 obtain a weighted biometric signal. In various examples, weighting may compute a magnitude of the biometric signal, such as a numerical value, that may be used to determine emotional state. Numerical weighting may include scaling a measured biometric signal, multiplying the biometric signal by a numerical weight, or similar. Any suitable scale may be used for weighting, such as 0-100, 1-5, 0 or 1, high/medium/low, or similar. Weighting may be used to give a measured biometric characteristic of the wearer of the headset a particular influence on emotion detection.

The biometric signal 114 is weighted based on the facial movement determined from the facial motion signal 112. For example, facial movement may negatively correlate to the suitability of using electromyography for emotion detection. That is, electromyography may be less reliable in determining emotional state to the degree that there is facial movement because, for example, an electromyography sensor may move or separate from the wearer's skin. As such, an electromyography signal may be weighted so that it is given increased influence on the determination of emotional state with decreased facial movement. For example, an electromyography signal may be weighted inversely proportionally to an amount of facial movement determined by motion analysis. In another example, an electromyography signal may be given no influence when facial movement exceeds the threshold amount of movement and may be given full influence when facial movement does not exceed the threshold amount of movement.

In another example, facial movement may positively correlate to suitability of the use of speech or other vocalization for emotion detection. That is, facial movement may indicate that vocalization may be useful in determining emotional state. As such, a vocalization signal may be weighted so that it is given increased influence on the determination of emotional state with increased facial movement determined by image analysis. For example, a vocalization signal may be given no influence or weight when facial movement is less than a threshold amount and may be given full influence or weight when facial movement exceeds the threshold amount. In another example, a vocalization signal may be weighted proportionally to an amount of facial movement.

Moreover, vocalization may cause facial movements that reduce the accuracy of certain biometric sensors, such as an electromyography sensor, a camera, or an eye sensor, in emotion determination. Speech and other vocalization often affect the shape of the face and the underlying musculature. Hence, vocalization may reduce the predictive effectiveness of sensors that directly measure facial movement. As such, when vocalization is detected, whether by image analysis or audio analysis, the influence of a vocalization signal may be increased at the same time that the influence of an electromyography signal, an image signal, and/or an eye signal is decreased.

The emotional state determination instructions 110 use the weighted biometric signal to determine an emotional state of the wearer of the headset. The weighted biometric signal may be input into a function that determines emotional state with reference to facial action units (FAU). In another example, the weighted biometric signal may be input into an artificial neural network (ANN) that has been trained to output emotional state.

An example FAU encoding scheme is as follows in Table 1.

TABLE 1

| Emotion | Action Unit (AU) |
| --- | --- |
| Neutral | None |
| Happy | Cheek Raiser |
| | Lip Corner Pulled |
| | Lips Part |
| Fear | Inner Brow Raiser |
| | Outer Brow Raiser |
| | Brow Lower |
| | Upper Eyelid Raiser |
| | Lip Stretcher |
| | Lips Part |
| Sad | Inner Brow Raiser |
| | Brow Lower |
| | Lip Corner Depressor |
| | Chin Raiser |
| Contempt | Dimple |
| Surprise | Inner Brow Raiser |
| | Outer Brow Raiser |
| | Upper Eyelid Raiser |
| | Jaw Drop |
| Anger | Brow Lower |
| | Upper Eyelid Raiser |
| | Eyelid Tighten |
| | Chin Raiser |
| | Lip Tighten |
| | Lip Pressor |
| Disgust | Nose Wrinkle |
| | Upper Lip Raiser |
| | Lips Part |

Biometric sensors that directly measure facial movement (e.g., electromyography sensor, camera, eye sensor) may correlate to action units as follows in Table 2.

TABLE 2

| Action Unit (AU) | Biometric Sensor |
|---|---|
| Inner Brow Raiser | EMG Sensor |
| Outer Brow Raiser | EMG Sensor |
| Brow Lower | EMG Sensor |
| Upper Eyelid Raiser | Eye Sensor |
| Cheek Raiser | EMG Sensor |
| Eyelid Tighten | Eye Sensor |
| Nose Wrinkle | EMG Sensor |
| Upper Lip Raiser | Camera |
| Lip Corner Puller | Camera |
| Dimple | Camera |
| Lip Corner Depressor | Camera |
| Chin Raiser | Camera |
| Lip Stretcher | Camera |
| Lip Tighten | Camera |
| Lip Pressor | Camera |
| Lips Part | Camera |
| Jaw Drop | Camera |

Any of such correlations may be provided in the emotional state determination, explicitly, as through a deterministic function, or implicitly, such as via an ANN.

For example, an FAU function may apply weights to camera, EMG sensor, and eye sensor signals to obtain weighted camera, electromyography, and eye signals. Such weightings may be applied based on a facial motion signal, as shown in Table 3. The weighted camera, electromyography, and eye signals may be applied to obtain correspondingly weighted action units, via Table 2. Then, the weighted action units may be combined to obtain correspondingly weighted emotion indicators, via Table 1. The strongest indicated emotion may be taken as the detected emotion. Alternatively, several emotions may be returned with numerical confidence values.

TABLE 3

| Detected Facial Motion | FAU Weight | Vocalization Weight |
|---|---|---|
| Low | High | Low |
| Medium | Medium | Medium |
| High | Low | High |

Vocalization, as determined from a microphone or similar sensor, may be treated with similar correlations. Acoustic features, such as pitch, energy and spectral coefficients, may be analyzed. Amplitude modification, prominence (e.g., a speaker's emphasis to draw attention to specific points of an utterance to express emotions or attitudes), and linguistic information may be considered. Table 3 shows that vocalizations may be weighted based on detected facial motion.

A result of acoustic feature analysis function may be combined with a result of an FAU function based on the weightings shown in Table 3 to arrive at a detected emotion.

Use of the biometric signal, as weighted by facial movement determined from motion analysis, may increase the accuracy of emotional state determination. This may be a result of weighting the biometric signal 114 using intelligence gained from facial movement represented in the facial motion signal 112. Hence, facial movement may cue how or if the biometric signal should be considered. It is contemplated that, in some instances, the biometric signal will be heavily discounted or even not considered, if, for example, the facial movement is extreme. For example, a high degree of motion blur in an image of the wearer's lip/jaw area may indicate that electromyography may be unreliable and that vocalization may be a more reliable indicator of emotional state. On the other hand, very low motion blur may indicate that electromyography may be reliable and that vocalization may be unhelpful to determine emotional state. In still another example, the presence of intense speech, as determined from the microphone, may indicate that direct facial movements measured by a camera or electromyographic sensor should be weighted less than speech analysis.

Figure 2:
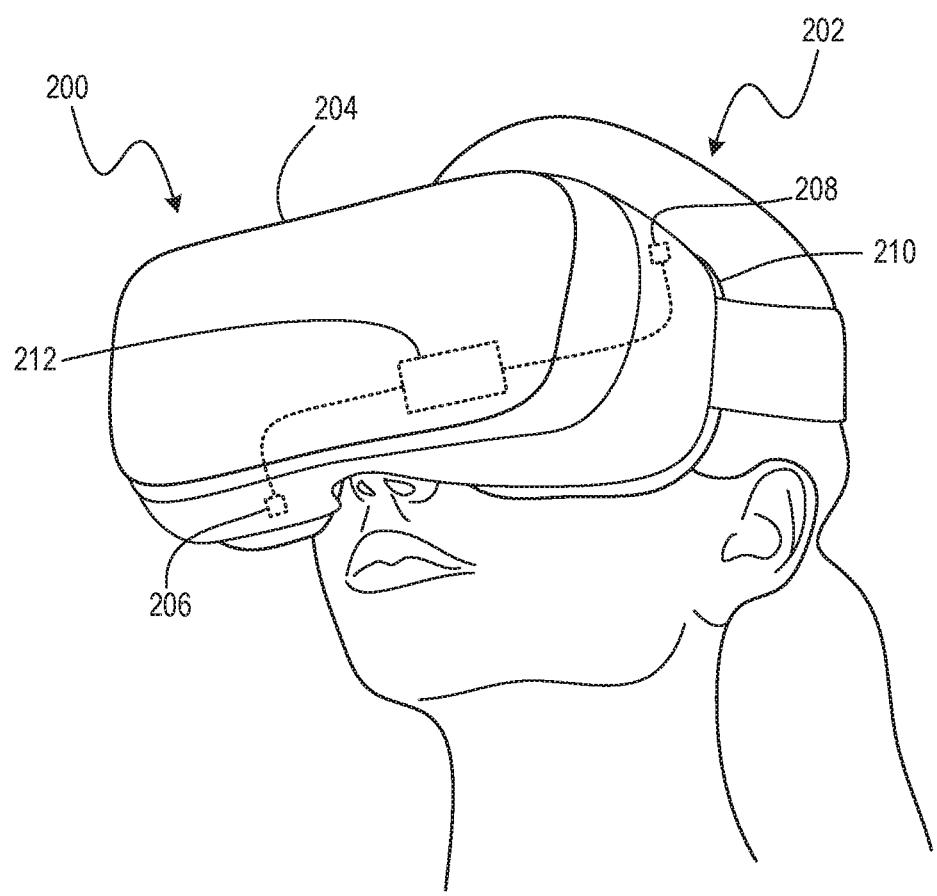
FIG. 2 is a perspective diagram of an example headset to determine emotional state from a headset wearer's facial movement and a biometric sensor at the headset.

FIG. 2 shows an example headset 200 worn by a person 202. The headset 200 may include a housing 204 that contains display electronics and optics to generate and output stereoscopic images to the wearer 202.

The headset 200 includes a facial motion sensor 206, such as a camera or microphone. A camera may be aimed towards the wearer's lip/jaw to directly capture facial movement. A microphone may be positioned near the wearer's mouth to capture his/her vocalizations, which may imply facial movement. The facial motion sensor 206 may also be considered a biometric sensor, in that captured images/sounds may also be used in emotion determination.

The headset 200 further includes a biometric sensor 208 to capture a biometric signal from the wearer. The sensor 208 may include an electromyography sensor, and eye sensor, or similar.

An electromyographic sensor may be positioned at or in the vicinity of a gasket 210 of the headset 200. The gasket 210 is for contacting the wearer's face to secure the headset 200 to the wearer 202 and block outside light from entering the wearer's eyes. The electromyographic sensor may be positioned at or near the gasket 210 to contact the wearer's skin near the eye. Any number of electromyographic sensors may be provided to measure movement of muscles around the wearer's eyes.

The headset 200 may further include a circuit 212 connected to the facial motion sensor 206 and the biometric sensor 208. The circuit 212 may be dedicated to capturing a facial motion signal from the facial motion sensor 206 and a biometric signal from the biometric sensor 208. In other examples, the circuit 212 may be a processor provided to the headset 200 to control stereographic imaging operations of the headset 200 and to capture signals from the sensors 206, 208.

As discussed elsewhere herein the circuit 212 may further determine an emotional state of the wearer 202 by processing the signals from the biometric sensor 208 based on a facial motion signal from the facial motion sensor 206. The facial motion signal may be instructive as to the manner of processing to be performed on the signal obtained from the biometric sensor 208. Further, the facial motion signal may also be used as a biometric signal to determine the emotional state of the wearer 202.

Figure 3:
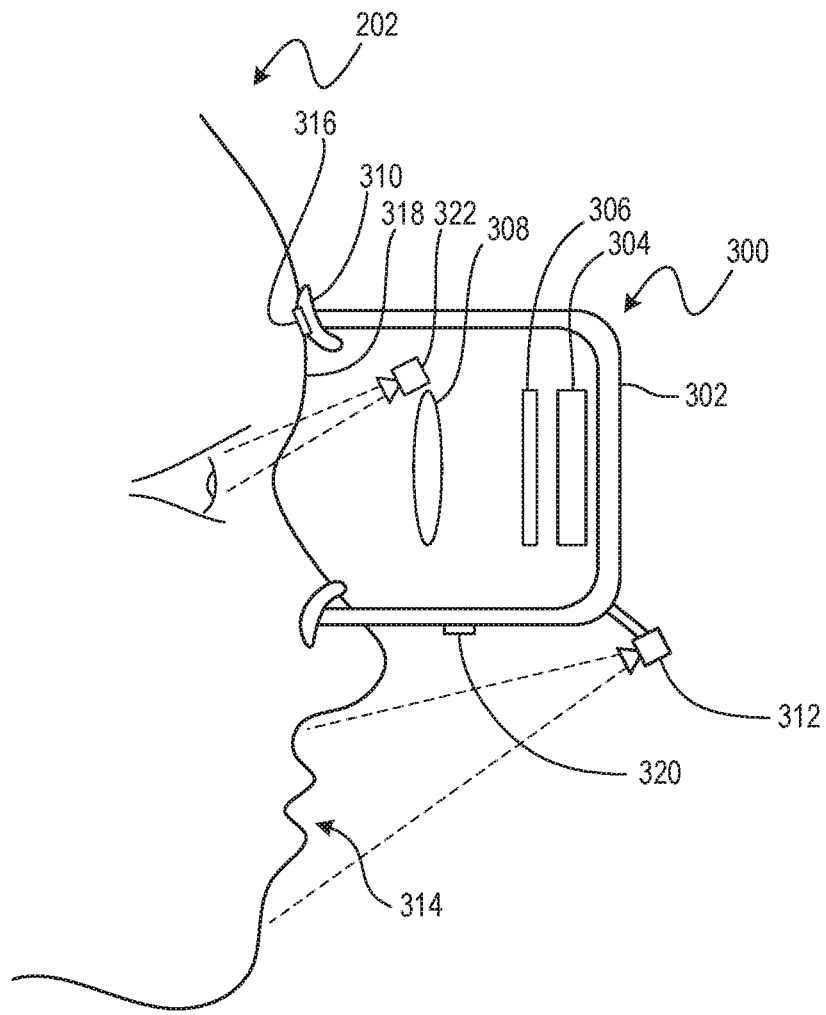
FIG. 3 is a side schematic diagram of an example headset to determine emotional state from a headset wearer's lip/jaw movement, an electromyography sensor, and an eye sensor.

As shown in FIG. 3, an example headset 300 includes a housing 302 that contains a circuit 304, a display 306, and optics 308 to generate stereoscopic images to allow a user 202 to engage in an XR experience. The headset 300 further includes a gasket 310 positioned at the housing to contact the wearer's face.

Features and aspects of the headset 300 may be similar or identical to the other headsets described herein. The other devices and headsets disclosed herein may be referenced for description not repeated here, with like terminology and/or like reference numerals indicating like components.

The headset 300 further includes a camera 312 aimed at the wearers lip/jaw area 314. The camera 312 is to capture images of the lip/jaw area 314. Such images may be used to determine to what extent, if any, a biometric sensor is to be used in emotion detection.

The headset 300 further includes a microphone 320 to detect vocalization of the wearer 202. In addition or alternatively to using images from the camera, vocalizations detected by the microphone may be used to determine to what extent, if any, a biometric sensor is to be used in emotion detection.

The headset 300 further includes an electromyographic sensor 316, which may be positioned at the gasket 310 so that a surface of the electromyographic sensor 316 contacts skin 318 around the eye of the wearer 202 to detect electrical impulses of a muscle near the eye.

The headset 300 may further include an eye sensor 322, such as a camera aimed at the wearer's eye, to detect pupil dilation, eyelid movement, eye movement, similar characteristic of the wearer 202.

The camera 312, electromyographic sensor 316, microphone 320, and eye sensor 322 are examples of biometric sensors that may be used in emotion detection. Motion of the wearer's face 202, as determined with the camera 312 and/or microphone 320, may be used to regulate the use or capture of biometric signals from the camera 312, electromyographic sensor 316, microphone 320, and eye sensor 322, so that an emotion of the wearer 202 may be accurately and efficiently detected.

Figure 4:
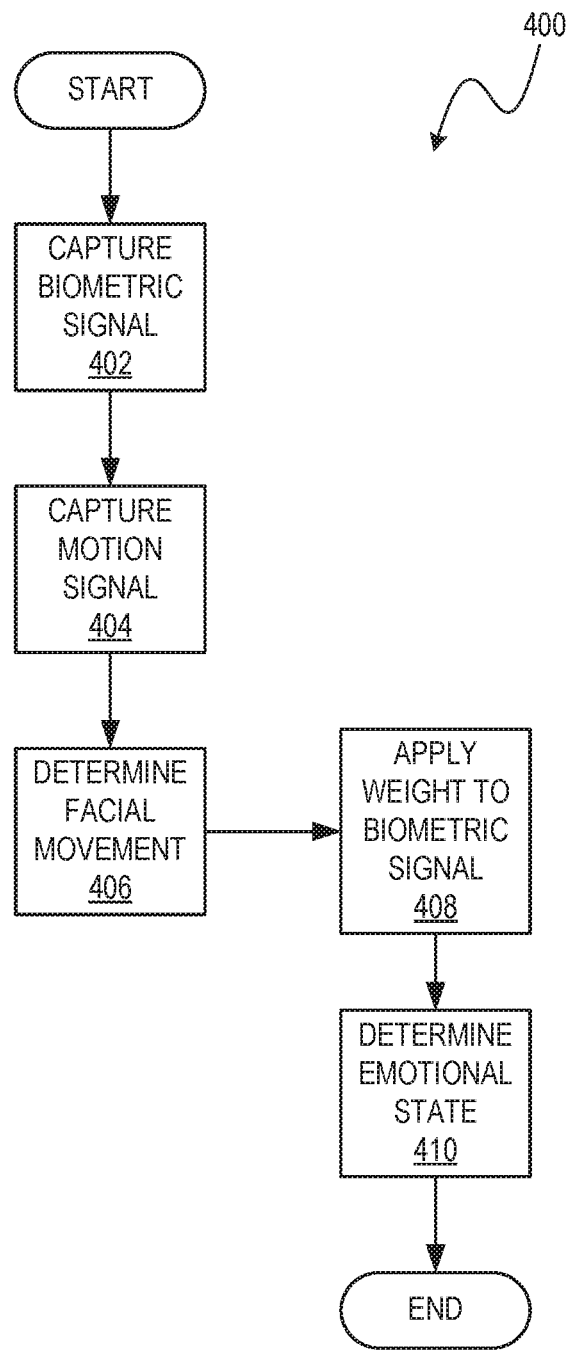
FIG. 4 is a flowchart of an example method to determine emotional state from a headset wearer's facial movement and a biometric sensor at a headset.

FIG. 4 shows an example method 400 to determine emotional state of a headset wearer from a biometric sensor as controlled by detected facial movement. The method 400 may be performed by any of the headsets or other devices discussed herein. The method 400 may be embodied as executable instructions.

At block 402, a biometric signal is captured from a sensor at a headset. Example sensors include a camera, an electromyography sensor, a microphone, a pupillometry sensor, and similar. The biometric signal reflects a physiological, bodily, or cognitive characteristic of the wearer of the headset.

At block 404, a facial motion signal is captured from another sensor associated with the headset, such as a camera or microphone. The facial motion signal indicates facial motion of the wearer of the headset. The facial motion signal may also indicate a physiological, bodily, or cognitive characteristic of the wearer of the headset.

At block 406, facial movement of the wearer of the headset may be determined based on the facial motion signal. Images of the wearer's jaw and/or lips may show facial movement. Facial movement may be detected by motion blur in an image signal. An amount of facial movement may be determined by quantifying the motion blur. Vocalizations may be processed using acoustic feature analysis to determine an extent of facial movement. For example, a high amplitude sound may indicate a high degree of facial movement.

The amount of facial movement may be represented as a numerical value to directly apply a weight to the biometric signal or may be used with comparison to a threshold amount of facial movement to determine the extent to apply the biometric signal. The amount of facial movement may inform a true/false flag that determines whether or not the biometric signal is used in emotion determination.

At block 408, the biometric signal is weighted based on the determined facial movement to obtain a weighted biometric signal. Weighting may include applying a numerical factor to the biometric signal, ignoring the biometric signal (e.g., by applying a zero weighting), or otherwise quantifying an influence of the biometric signal on determination of emotion of the wearer. For example, if the biometric signal includes an electromyographic signal, applying a weight to the biometric signal may include giving increased influence to the electromyographic signal with decreased facial movement. This may include weighting the electromyographic signal more heavily when less facial movement is detected, so as to reflect that the electromyographic signal may be more indicative of emotion when the wearer is relatively motionless. In another example, if the biometric signal includes a vocalization signal, applying a weight to the biometric signal may include giving increased influence to the vocalization signal with increased facial movement. This may include weighting the vocalization signal more heavily when greater facial movement is detected, so as to reflect that the vocalization signal may contain information that is of greater use when the wearer's face is moving.

At block 410, the weighted biometric signal is used to determine the emotional state of the wearer of the headset. The facial motion signal may also be taken as a biometric signal to determine emotional state. All available biometric signals, as may be weighted, may be applied to determine emotional state. This may include applying the weighted biometric signal to an FAU function, an ANN, or similar. Emotional state may be outputted as a list of emotions (e.g., neutral, happy, fear, sad, contempt, surprise, anger, and disgust) with associated confidence values.

Figure 5:
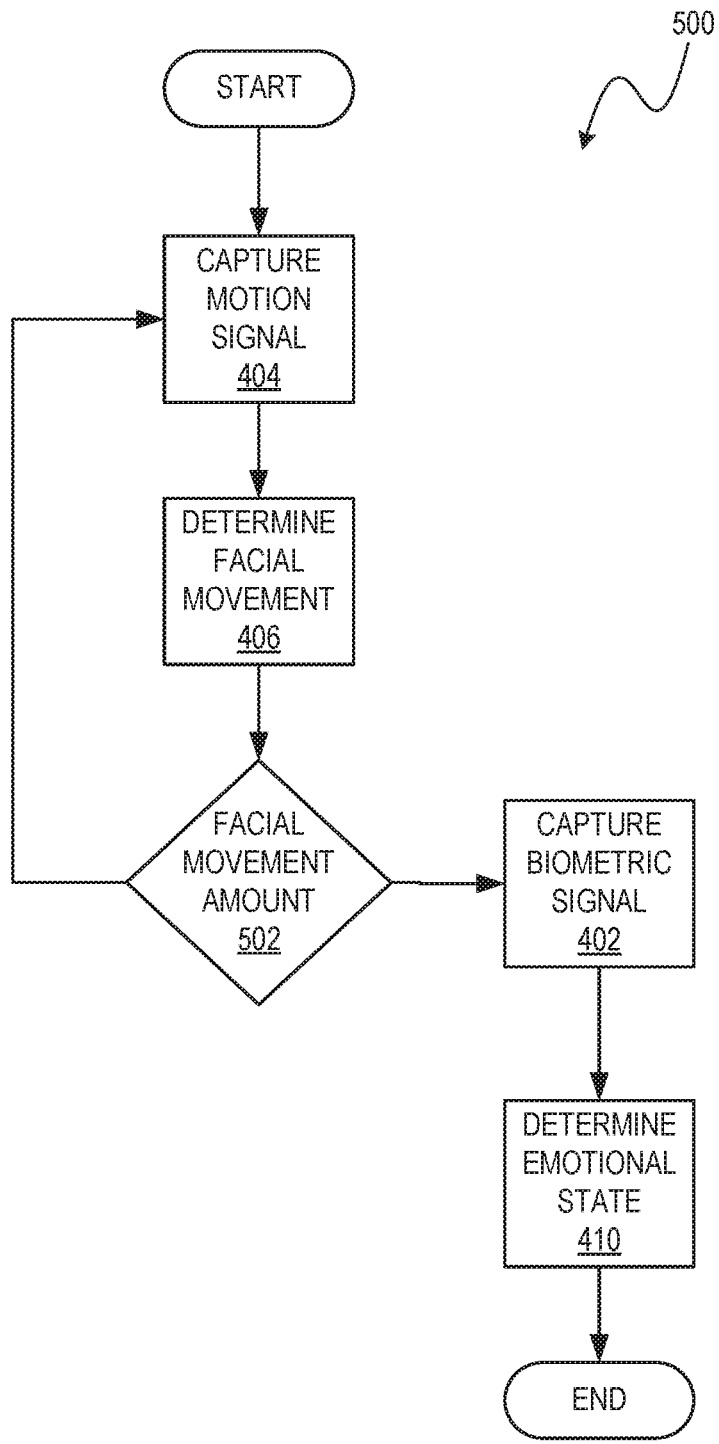
FIG. 5 is a flowchart of an example method to determine emotional state from a headset wearer's facial movement and a biometric sensor at a headset, in which an amount of facial movement is considered.

FIG. 5 shows an example method 500 to determine emotional state of a headset wearer from a biometric sensor as controlled by an amount of detected facial movement. The method 500 may be performed by any of the headsets or other devices discussed herein. The method 500 may be embodied as executable instructions.

The headset wearer's facial movement is determined from a captured facial motion signal at blocks 404, 406.

At block 502, capture of a biometric signal, at block 402, may be triggered by determined facial movement conforms to a predetermined amount of movement. Conformance to a predetermined amount of movement may reference a threshold amount that is exceed or not exceeded, depending on the specific biometric signal. For example, the predetermined amount of movement may be a maximum amount of movement, below which an electromyographic signal is captured. In another example, the predetermined amount of movement may be a minimum amount of movement, above which a vocalization signal is captured.

In other examples, the biometric signal is captured regardless of the amount of facial movement, and block 502 is used to determine whether or not the biometric signal is used in emotional state determination. That is, block 402 may come before block 502.

Block 502 may be considered a weighting of the biometric signal, in that the biometric signal is either used or not used depending on the outcome of block 502. This may be considered equivalent to assigning a weighting of 1 or 0.

Then, at block 410, emotional state of the wearer of the headset is determined using the biometric signal if facial movement is determined to be of suitable amount, via block 502.

Figure 6:
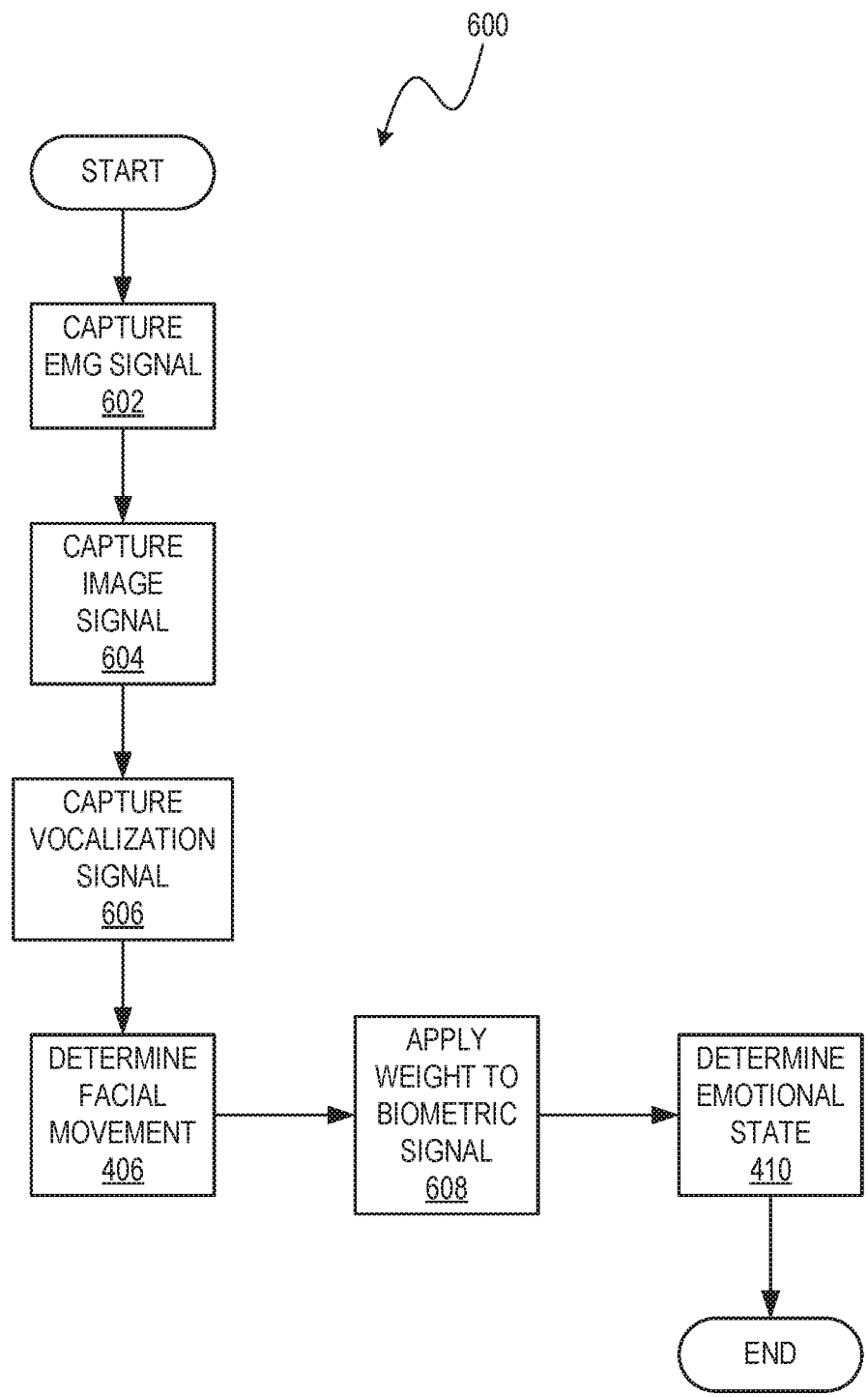
FIG. 6 is a flowchart of an example method to determine emotional state from a headset wearer's facial movement, vocalization, and electromyography.

FIG. 6 shows another example method 600 to determine emotional state of a headset wearer from a biometric sensor as controlled by an amount of detected facial movement. The method 600 may be performed by any of the headsets or other devices discussed herein. The method 600 may be embodied as executable instructions.

At block 602, an electromyographic signal is captured from a wearer of a headset. An electromyographic sensor in contact with the wearer's skin around the eye may be used.

At block 604, an image signal of the headset wearer's lip/jaw area is captured by a camera.

At block 606, a vocalization signal is captured from he wearer of the headset.

The headset wearer's facial movement is determined from a captured signal, at block 406. One or both of the image signal and the vocalization signal may be used to determined faction motion.

At block 608, a biometric signal is weighted based on the amount of facial movement. Any of the electromyographic signal, image signal, and vocalization signal may be considered a biometric signal. The amount of facial movement may be used apply a weighting to a biometric signal. The amount, presence, or absence of facial movement may be used to include or exclude a biometric signal for emotion determination.

Then, at block 410, the emotional state of the wearer of the headset is determined using the weighted biometric signal or signals.

Figure 7:
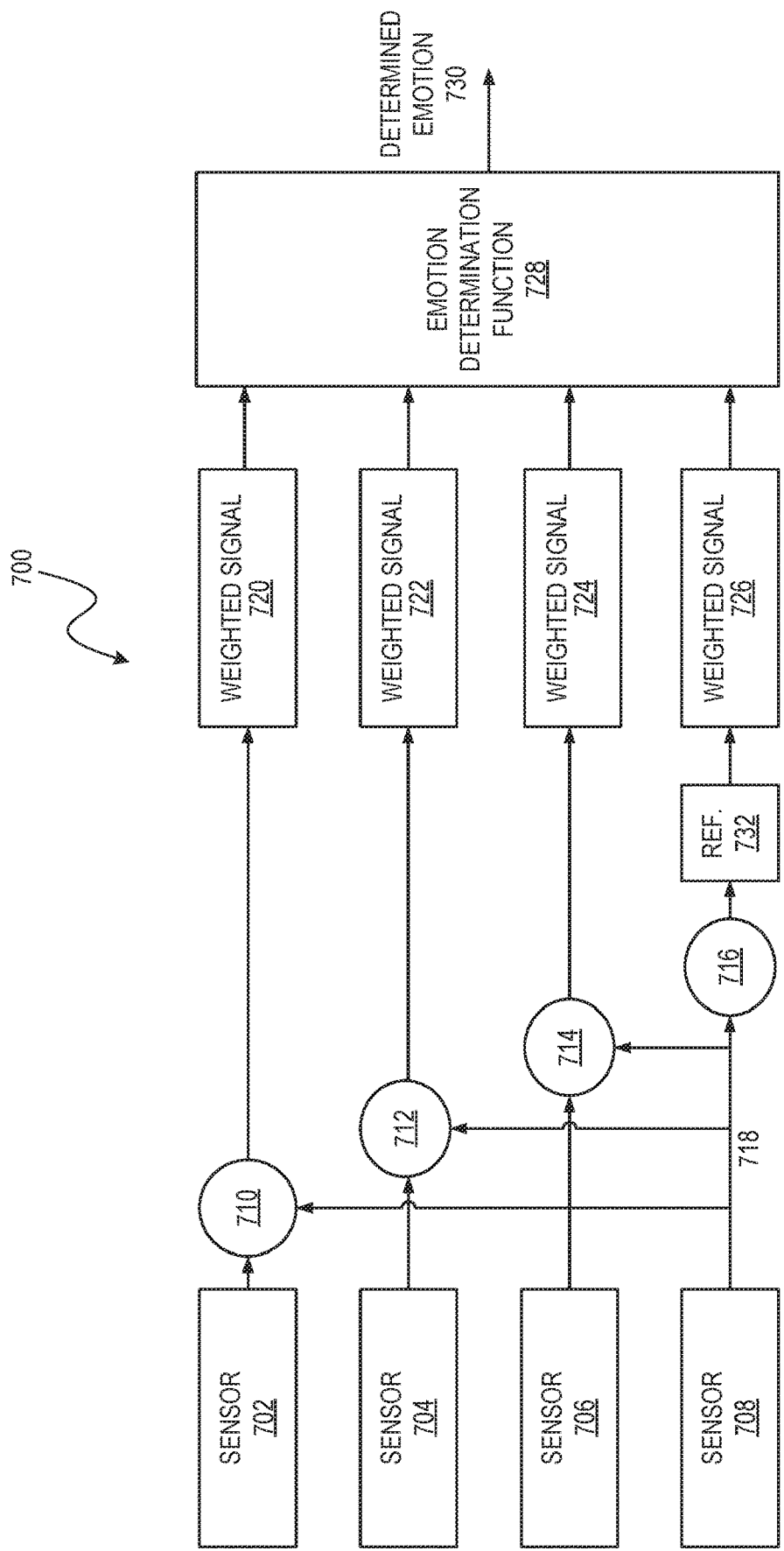
FIG. 7 is a schematic diagram of an example processing network to determine emotional state from a headset wearer's facial movement and various biometric sensors at a headset.

FIG. 7 shows an example processing network 700 to capture biometric sensor inputs and generate an emotion determination of a wearer of a stereographic headset. The processing network 700 may be used with any of the headsets, other devices, and methods described herein. The processing network 700 may be embodied as executable instructions.

A plurality of sensors 702-708, such as a camera, microphone, electromyographic sensor, and eye sensor may capture respective biometric signals from a wearer of a headset.

The biometric signals may be weighted by respective weight applicators 710-716 to obtain weighted biometric signals. A weight applicator 710-716 may convert signal into a numerical value, a true/false value, or similar. A weight applicator 710-716 may apply a weighting, may scale a biometric signal, or may apply another function to a biometric signal. A weight applicator 710-716 may compare a biometric signal to a threshold to generate a weighted biometric signal.

In addition to its source biometric signal, a weight applicator 710-714 may also take as input a facial motion signal 718 obtained from a sensor 708, such as a camera aimed at the headset wearer's lip and jaw area, a microphone, or similar. The sensor 708 may be considered a facial motion sensor. The facial motion signal 718 may be used to apply a weight to another biometric signal by, for example, setting a weighting to apply, setting a threshold value, or similar.

Output of the weight applicators 710-716 are respective weighted signals 720-726 which are provided to an emotion determination function 728.

The emotion determination function 728 may include a FAC function, a speech/vocalization analysis function, an ANN, and/or similar function. The emotion determination function 728 outputs a determined emotion 730 of the headset wearer. The determined emotion 730 may be outputted to, for example, an XR avatar of the wearer (e.g., a descriptor or avatar facial expression), a user interface of a computing device to which the headset is connected, a log file, or similar. Indications of determined emotions 730 may include text (e.g., the emotions listed in Table 1), graphics, images, animation, or similar.

The processing network 700 may further include a reference selector 732. The reference selector 732 selects a frame of reference for biometric signal analysis based on a facial movement signal 718.

A biometric signal may be continuously captured by a sensor 702-708. The biometric signal may be time coded. Several sensors 702-708 may be time coded with the same clock so that their signals are synchronized.

The reference selector 732 may refer to the facial movement signal 718 to determine a reference time to select the biometric signal for use in emotion determination. For example, the sensors 702-708 may capture signals at different rates and the facial movement signal 718 may have the lowest frequency. Hence, the facial movement signal 718 may dictate the rate at which biometric signals are processed.

The reference selector 732 may detect an event based on the facial movement signal 718. Detection of the event may trigger capture of a biometric signal by another sensor 702-706. For example, the facial motion sensor 708 may be a camera. A detected event may be based on FAU analysis using an image signal from the camera. Initial detection of an emotion using the camera may trigger capture of another biometric signal using another of the sensors 702-706. In another example, a degree of motion is determined to be an event that triggers biometric signal capture, as shown in FIG. 5.

The reference selector 732 may set a capture frequency of a biometric signal based on an event detected based on the facial motion signal. For example, increased facial movement may increase the frequency of capture of samples of a biometric signal, such as vocalization, that positively correlates facial movement to emotion. That is, a first sample rate (frequency) may be used in the event of low facial movement and a second sample rate may be used in the event of high facial movement. The first and second sampling rates are different. In the example of vocalization, low facial movement may trigger a sample rate of 16 kHz and high facial movement may trigger a sample rate of 44 kHz. In another example, low facial movement may increase a sample rate of a captured electromyographic signal, whereas high facial movement may trigger a decrease in such a sample rate.

It should be apparent from the above, that motion data of a headset wearer's face, such as captured by a camera or microphone, may be used to facilitate the processing of data from a biometric sensor to increase accuracy of emotion detection, assist in determining cognitive/mental load, and reduce instances of miscommunication or misunderstanding in XR experiences.

It should be recognized that features and aspects of the various examples provided above can be combined into further examples that also fall within the scope of the present disclosure. In addition, the figures are not to scale and may have size and shape exaggerated for illustrative purposes.

The invention claimed is:

1. A non-transitory machine-readable medium comprising instructions executable by a processor to:
capture a biometric signal from a biometric sensor at a headset that includes a stereoscopic display;
capture a facial motion signal from a facial motion sensor associated with the headset;
determine facial movement of a wearer of the headset based on the facial motion signal;
apply a weight to the biometric signal based on the facial movement to obtain a weighted biometric signal; and
use the weighted biometric signal to determine an emotional state of the wearer.

2. The medium of claim 1, wherein:
the biometric sensor comprises an electromyography sensor;
the biometric signal comprises an indication of facial muscle movement of the wearer; and the weighted biometric signal is given increased influence on determination of the emotional state of the wearer with decreased facial movement.

3. The medium of claim 1, wherein the instructions are to apply a weight to the biometric signal based on comparison of the facial movement to a predetermined amount of movement.

4. The medium of claim 1, wherein the instructions are further to:
capture an eye signal from an eye sensor at the headset;
use the eye signal, in addition to the weighted biometric signal, to determine the emotional state of the wearer.

5. The medium of claim 1, wherein the instructions are further to:
continuously capture the biometric signal;
determine a reference time to select the biometric signal based on the facial movement; and
use the biometric signal at the reference time to determine the emotional state of the wearer.

6. The medium of claim 1, wherein capture of the biometric signal is triggered by an event detected based on the facial motion signal.

7. The medium of claim 1, wherein a frequency of capture of the biometric signal is determined from an event detected based on the facial motion signal.

8. A headset comprising:
a stereoscopic display;
a facial motion sensor;
a biometric sensor; and
a processor to capture a facial motion signal from the facial motion sensor and to capture a biometric signal from the biometric sensor, the processor to apply a weight to the biometric signal based on the facial motion sensor to detect an emotion of a wearer of the headset.

9. The headset of claim 8, wherein the facial motion sensor comprises a camera or a microphone.

10. The headset of claim 8, wherein the processor is further to capture an additional biometric signal from the facial motion sensor, and wherein the processor is further to apply an additional weight to the additional biometric signal to detect the emotion of the wearer of the headset.

11. The headset of claim 8, wherein the biometric sensor comprises an electromyography sensor.

12. The headset of claim 8, wherein the processor is to apply a numerical weight to the biometric sensor based on the facial motion sensor.

13. The headset of claim 8, wherein the processor is to apply a weighted biometric signal to a set of facial action units to the detect the emotion of the wearer of the headset.

14. A method comprising:
capturing a biometric signal from a biometric sensor at a headset that includes a stereoscopic display;
capturing a facial motion signal from a facial motion sensor associated with the headset;
applying a weight to the biometric signal based on the facial motion signal to obtain a weighted biometric signal;
applying the weighted biometric signal to determine an emotional state of a wearer of the headset; and
outputting an indication of the emotional state.

15. The method of claim 14, wherein:
capturing the biometric signal comprises capturing images of a lip and jaw area of the wearer, capturing vocalizations of the wearer, and capturing an electromyography signal from a muscle at an eye of the wearer; and
capturing the facial motion signal comprises capturing images of the lip and jaw area of the wearer, capturing vocalizations of the wearer, or capturing both images of the lip and jaw area of the wearer and vocalizations of the wearer.

* * * * *